(12) United States Patent
Güntner et al.

(10) Patent No.: US 10,667,722 B2
(45) Date of Patent: Jun. 2, 2020

(54) FAT BURNING ANALYZER

(71) Applicant: ETH Zürich, Zürich, ETH Zentrum (CH)

(72) Inventors: Andreas T. Güntner, Zürich (CH); Sotiris E. Pratsinis, Zürich (CH)

(73) Assignee: ETH ZÜRICH, Zürich (CH)

( * ) Notice: Subject to any disclaimer, the term of this patent is extended or adjusted under 35 U.S.C. 154(b) by 191 days.

(21) Appl. No.: 15/825,671

(22) Filed: Nov. 29, 2017

(65) Prior Publication Data

US 2018/0146888 A1   May 31, 2018

(30) Foreign Application Priority Data

Nov. 29, 2016   (CH) ..................................... 1567/16

(51) Int. Cl.
*A61B 5/083*   (2006.01)
*G01N 33/497*   (2006.01)
(Continued)

(52) U.S. Cl.
CPC ............ *A61B 5/0836* (2013.01); *A61B 5/083* (2013.01); *A61B 5/0833* (2013.01);
(Continued)

(58) Field of Classification Search
CPC ..... A61B 5/0836; A61B 5/083; A61B 5/0833; A61B 5/082; A61B 5/0873; A61B 5/0878;
(Continued)

(56) References Cited

U.S. PATENT DOCUMENTS

2014/0228698 A1\* 8/2014 Roeck ................. G01N 33/497
600/532
2014/0358019 A1\* 12/2014 Johnson ................. A61B 5/097
600/532

(Continued)

FOREIGN PATENT DOCUMENTS

JP     2001-349888    12/2001
JP     2 762 882      8/2014
(Continued)

OTHER PUBLICATIONS

Toyooka, et al., "A prototype portable breath acetone analyzer for monitoring fat loss", Journal of Breath Research, Jul. 24, 2013, IOP Publishing, 8 pages.
(Continued)

*Primary Examiner* — Nimeshkumar D Patel
*Assistant Examiner* — Suman K Nath
(74) *Attorney, Agent, or Firm* — Rankin, Hill & Clark LLP (57) ABSTRACT

The fat burning analyzer includes a sampling part, an analysis unit and a processing unit. The sampling part collects a breath sample from the user, information on the conditions of the breath sample collection, and provides a sampling signal correlated to the collection condition of the breath sample. The analysis unit provides a detection signal corresponding to an acetone concentration in the collected breath sample and, as such, provides information on the breath acetone of the user (during exercise or resting). The processing unit receives the sampling signal and/or detection signal, and evaluates the sampling signal and/or the detection signal. The evaluation provides information correlated to the fat burning intensity of the user. These information can be provided as an output signal by the processing unit. Accordingly, the processing unit is equipped to provide an (Continued)

output signal correlated to the fat burning intensity of the user.

27 Claims, 3 Drawing Sheets

(51) Int. Cl.
*A61B 5/08* (2006.01)
*A61B 5/087* (2006.01)
*A61B 5/097* (2006.01)

(52) U.S. Cl.
CPC ............ *G01N 33/497* (2013.01); *A61B 5/082* (2013.01); *A61B 5/0873* (2013.01); *A61B 5/0878* (2013.01); *A61B 5/097* (2013.01)

(58) Field of Classification Search
CPC .. A61B 5/097; G01N 33/497; A61K 2300/00; A61K 31/4164
USPC .......................................................... 73/23.3
See application file for complete search history.

(56) References Cited

U.S. PATENT DOCUMENTS

| | | | |
|---|---|---|---|
| 2015/0032019 A1* | 1/2015 | Acker | A61B 5/082 600/532 |
| 2016/0341716 A1* | 11/2016 | Rodriguez | G01N 33/497 |
| 2017/0074857 A1* | 3/2017 | Dennis | G01N 33/497 |
| 2017/0191953 A1* | 7/2017 | Rigas | G01N 27/126 |

FOREIGN PATENT DOCUMENTS

| | | |
|---|---|---|
| WO | 01/93743 | 12/2001 |
| WO | 2013/003429 | 1/2013 |

OTHER PUBLICATIONS

Switzerland Search Report dated Mar. 20, 2017, Application No. 15672016, 4 pages.

European Office Action dated Jul. 30, 2019, Application No. 17 204 314.3, 4 pages.

* cited by examiner

FAT BURNING ANALYZER

BACKGROUND OF THE INVENTION

Field of the Invention

The invention generally relates to a breath analyser and, more specifically, relates to a portable fat burning analyser.

Description of Related Art

Obesity is one of the major health challenges of modern society. Online monitoring of the fat burn rate would offer key advantages for efficient weight loss as physical exercise and diet can be tailored individually and monitored in real-time. Breath acetone detection has the potential to provide such a non-invasive method to monitor the fat metabolism process, as the ketone body acetone is a by-product of the lipolysis. Breath analysis by chemo-resistive metal-oxide gas sensors is a very promising method due to low fabrication costs, simple applicability and easy integrability into portable devices because of their small sizes.

In Analytical Chemistry 2010, 82, 3581-3587 an acetone selective sensor is disclosed capable to detect acetone.

A prototyped portable acetone analyser was disclosed in Toyooka et al., Journal of Breath Research, 2013; 7:036005. Breath acetone was measured by an array of two semiconductor based, chemo-resistive metal-oxide gas sensors, made of Pt-doped $WO_3$ (high sensitivity to acetone) and of $SnO_2$ (equally sensitive towards acetone and interference gases), respectively. A significant increase of breath acetone concentration (average concentration from 1.3 to 2.1 parts per million (ppm)) was in agreement to a loss of body fat (measured by a bath scale) when exercise and controlled caloric intake were combined. However, detection accuracy with an error of ±400 ppb for a detected acetone concentration of 600 ppb is a drawback of this prototype, wherein the conditions of the measurements are not controlled. The similar holds true for a portable electronic device as discloses in EP 2762882. EP 2762882 discloses a compensator for compensating for the effect of variations in the amount of the exhaled breath passing the portable device. Such a compensation reduces the influence of the dilution of the exhaled breath with surrounding air. A further apparatus for measuring body fat burning amount is known from JP 2001349888 where the use breathes onto the apparatus and indicates the breathing by pressing a button. A respiratory breath ketone analyser is known from WO 01/93743, where the exhaled air is preconditioned, e.g. dried.

SUMMARY OF THE INVENTION

It is therefore an object of the invention to create a fat burning analyser with improved configuration for controlled monitoring of the fat burning intensity of a user from the user's breath essentially immediately, which overcomes the disadvantages mentioned above and/or to provide a non-invasive method and/or device to monitor the fat burning intensity of the user and/or to support the user at his diet.

The fat burning analyser can be portable, meaning that the fat burning analyser is light enough to be transported by an adult. The fat burning analyser is equipped for monitoring of the fat burning intensity of a user from the users breath, wherein the monitoring can be performed online, meaning essentially instantaneously. Furthermore, the fat burning intensity can be performed in a non-invasive manner. Additionally, the monitoring can be performed when the user is exercising, dieting and/or resting.

The analyser comprises at least a sampling part, an analysis unit and a processing unit.

The sampling part is equipped for collecting a breath sample from the user (during exercise, diet or resting). Furthermore, the sampling part is equipped for collecting information on the conditions of the breath sample collection. Additionally, the sampling part is equipped to provide a sampling signal correlated to the collection condition of the breath sample. In other words: The sampling conditions in the sampling part can be monitored and the corresponding sampling signal (including information on sampling) is provided by the sampling part. Thereby, the collection of the breath sample may also mean recognition of the breath sample. Accordingly, the sampling part can be equipped for recognising and/or collecting a breath sample. Hence the collection condition can be monitored and controlled.

The sampling signal can be capable of indicating and can be equipped to indicate the beginning of the end-tidal portion of the breath sample. This allows to analyse specifically the end-tidal portion of the breath sample, which includes relevant information on the fat burning intensity of the user. The indication of the end-tidal portion of the breath sample can be an estimation, for example because the lung volume of the each user can vary. The indication of the end-tidal portion of the breath sample can also be a rather precise/accurate determination, for example by measuring the CO2-concentration of the breath sample.

The indication of the end-tidal breath sample can enable a control of the collection conditions, in particular the collection conditions of the end-tidal portion of the breath sample.

The fat burning intensity of the user can be provided reproducibly based on the information of the collection condition provided by the sampling signal. In other words: Due to the sampling signal the collection of the end-tidal portion of the breath sample can be indicated. Accordingly, the detection signal can be focused on the relevant end-tidal portion of the breath sample. Inaccuracy of the detection signal due to none controlled sample collection can be minimised, leading to the reproducibility of the fat burning intensity based on the information of the collection condition provided by the sampling signal.

The analysis unit is equipped to provide a detection signal corresponding to an acetone presence in the collected breath sample. As the detection signal corresponds to the acetone presence in the breath sample the analysis unit can provide information on the breath acetone of the user (during exercise, diet or resting). Thereby, the detection signal can correspond to a quantitative and/or qualitative information of the acetone presence, meaning that the quantified concentration and/or the qualitative presence of acetone can be encoded in the detection signal. Furthermore, it is possible that the detection signal includes encoded information, for example in form of a signal, in particular a resistance value, of a sensor or a detector. The detection signal i.e., encoded information, can be processes in the processing unit. The detection signal can depend on the acetone presence, in particular on the acetone concentration.

The processing unit is equipped to receive the sampling signal and/or detection signal. Furthermore, the processing unit is equipped to evaluate the sampling signal and/or the detection signal. The evaluation provides information correlated to the fat burning intensity of the user. These information can be provided as an output signal by the processing unit. Accordingly, the processing unit is equipped to provide an output signal correlated to the fat burning intensity of the user. In other words: The analysis unit can provide a detection signal that includes information on the acetone presence and the processing unit is equipped to evaluate the correlation of the detection signal, in particular by taking into account further information, for example obtained from the sampling signal.

The fat burning intensity can either correspond to a binary status information like fat burning: yes/no, or it can correspond to the degree of the fat burning.

The analysis unit can be equipped to collect and/or provide the detection signal corresponding to an acetone presence in the collected breath sample.

The sampling part can include a sampling chamber for collecting the breath sample. The sampling chamber can be a cavity i.e., a compartment, into which the user can breathe. Therefore, the breath sample can be collected in the sampling chamber in the sampling part.

The sampling chamber can be designed as sampler tube, providing a tube shaped compartment for collecting the breath sample. The sampling chamber can include Teflon®, in particular at an inner surface of the sampling chamber can include and/or consist of Teflon®, and/or a material inhibiting the adsorption of the analyte, in particular acetone. Hence, the sampling signal is essentially not influenced by the adsorption of acetone or an analyte essential for determining the sampling conditions, e.g. CO2. Additionally, an influence on the detection signal might by minimized, as the adsorption of the analyte, in particular acetone, is inhibited and accordingly the information on the acetone presence is essentially not influenced.

The sampling part, in particular the sampling chamber, in particular the sampler tube can be designed as a calibrated buffering tube. Such a calibrated buffering tube can be adapted for measurement of mouth pressure. The measurement of the mouth pressure of the user can provide further information on the sampling condition.

The sampling part, in particular the sampling chamber, in particular the sampler tube can be equipped for buffering the breath sample. Buffering in this context means that the breath sample is hold, kept or stored in the sampling part, in particular in the sampling chamber, in particular in the sampler tube, for a time proceeding the time of the breath pulse originating from the user breathing into the fat burning analyser. With such a buffering the detection time of the breath sample can be prolonged which might lead to in an increase of reproducibility of the determination of the fat burning intensity.

The sampling part, in particular the sampling chamber, in particular the sampler tube can be at least 30 cm long. Such a long sampling part enables to keep the end-tidal fraction of the breath pulse inside the sampling part. This can allow for a prolonged sampling time that can result in a better reproducibility of the determination of the fat burning intensity. Nevertheless, the sampling part, in particular the sampling chamber, in particular the sampler tube, can also be shorter than 30 cm to reduce size of the sampling part and the fat burning analyser.

The sampling part can include an inlet and/or an outlet, in particular the sampling chamber can include the inlet and/or outlet. The user can breathe through the inlet into the sampling part for collecting the breath sample. The breath flowing through the sampling part, meaning breathed into the sampling part, is guided from the inlet to the outlet. The outlet allows air to be pushed out of the sampling part. This allows mixed end-tidal portion of the breath sample to remain in the sampling part. Thereby, the positioning of the outlet of the sampling part can be different from the positioning of an inlet of the analysis unit. In a particular embodiment the inlet can correspond to the outlet. The sampling part can be a through flow part and/or a dead-end part.

The end-tidal portion and/or mixed end-tidal portion of a breath i.e., of an exhalation (breath sample) includes an elevated acetone concentration, also called endogenous acetone, compared to the surrounding air. Endogenous means generated in the body of the user. The endogenous acetone gets into the breath sample through interaction of the air with blood in alveolar membrane. The end-tidal portion of the breath sample has a carbon dioxide (CO2 or $CO_2$) concentration higher 3% of the total volume of the breath sample.

The sampling part can include at least one sensor equipped for providing information on the condition of the breath sample collection, as described above. The type of information naturally depends on the type of sensor in the sampling part. In particular, the sensor can be, respectively can be designed as, a pressure sensor, a humidity sensor, a flow sensor, a temperature sensor and/or a CO2-sensor. Hence the sensor can provide information on the pressure, humidity, flow, temperature and/or the CO2 concentration of collection of the breath sample.

The sensor can be arranged between the inlet and the outlet to provide valuable sampling information about the condition of the sample collection. In particular, the sensor can be arranged close to the inlet and/or outlet, allow for precise information at the entrance or exit of the breath sample in the sampling part of the fat burning analyser.

The sensor can be arranged directly in the buffering volume. The buffering volume can correlate with the volume of the sampling chamber.

The sensor can be commercially available. The functional operation of the fat burning analyser can be improved by the operating principle of the described fat burning analyser.

The sensor can be equipped to provide sampling signal. Depending on the particular sensor used/applied, the sampling signal can include information on the pressure, humidity and/or the CO2 concentration during breath sample collection. This can enable the recognition or the indication of the breath sample pulse.

The sampling part can be equipped for enabling the user to reach and/or maintain a target value and/or target duration for collection of a breath sample of the user. In particular, the user can be enabled to reach and/or maintain a target value and/or target duration for collection of a breath sample by notifying the information of collection condition and/or the target value and/or duration for the breath sample collection. The information can already be processed in order to simplify the reaching and/or maintaining of a target value and/or target duration for the user.

The sampling signal can include information on at least one of the following quantities: pressure, time/duration of the breath sample, temperature, volume of the breath sample and flow of the breath sample, in particular information on a CO2-concentration and/or humidity of the breath sample. From at least one of these quantities the beginning of the end-tidal portion of the breath sample can be indicated or determined/estimate.

The sampling signal can trigger the detection signal. The triggering of the detection signal can be correlated with the indication of the end-tidal portion of the breath sample. In other words: The triggering of the detection i.e., the detection signal, can be linked to the collection of the breath sample, in particular to the end-tidal portion of the breath sample.

The sampling signal can be capable of indicating a breath sample, in particular the end-tidal portion of the breath sample. Accordingly, the breath sample can be detected after being indicated. This enable a reliable detection of the breath sample and a corresponding output of the fast burning intensity of the user.

The sampling signal can also be utilised for controlling and/or correction of the detection signal.

The processing unit can be equipped to recognise the breath sample due to the sampling signal and its comparison with corresponding target values. This enables a comparative evaluation of the breath sample.

The target value is defined as a sampling value or a collection value. The target value can be defined as at least one of the following conditions: a certain pressure or pressure difference in the sampling part measured by the pressure sensor, a certain humidity measured by the humidity sensor indicating the beginning of the breath pulse, a certain $CO_2$-level or $CO_2$ concentration indicating the end-tidal breath portion, a certain flow measured by the flow sensor indicating the volume of the breath pulse, a certain temperature measured by the temperature sensor indicating the temperature of the breath pulse. Obviously, also further parameter indication either the beginning of the breath pulse and/or the end-tidal breath portion can be measured or monitored or evaluated by the sampling part or the processing unit.

The target value for the pressure can be a pressure drop of 980 Pa. The target value for the humidity can be 70% relative humidity RH or more. The target value for the $CO_2$ level can be 3% or higher.

The target duration of the breath pulse corresponding to the breath sampling time can be 30 seconds or longer. Such a target duration can be kept easily by the user with an airway pressure of 980 Pa. The breath sampling time can also be shorter than 30 seconds.

Information can be notified on a monitor, by an audio signal and/or by vibration. In particular, it is possible that the target value and the real time information of the breath sampling condition is displayed simultaneously, enabling the user to reach and/or maintain the target value. The simultaneous display could be realized by a colour coded display, indication the reaching of the target value.

The sampling signal can enable the user to reach and/or maintain the target value and/or the duration for collection of the breath sample. As described above the sampling part can provide the sampling signal that can be displayed indicating the reaching and/or maintaining the target value or duration. The sampling signal can notified on a monitor, by an audio signal, a visual signal and/or by vibration.

The sampling signal can include information on an exhaling intensity of the user, on the portion of the breath sample to be analysed and/or on the sampling condition of the breath sample. As pointed out before, the information can be obtained from a sensor as described. Thereby, the exhaling intensity can be determined by the pressure sensor, the portion of the breath sample, for example the end-tidal portion and/or the mixed end-tidal portion, can be determined by the $CO_2$-sensor, and the sampling condition of the breath sample can be determined by the humidity sensor. These information of the breath sampling condition can be displayed as described above.

In other words: The sensor can be designed as a pressure sensor, wherein the pressure sensor can be arranged in the sampling part and is capable of providing information on the exhalation intensity or exhalation volume of the user. This information can be obtained for the pressure or pressure change in the sampling part while the user is breathing into the fat burning analyser. This breathing into the fat burning analyser generates a breath pulse.

The volume of the breath sample can be determined from the pressure and the duration time of the breath sample.

The sensor can be designed as a humidity sensor, wherein the humidity sensor can be arranged in the sampling part and is capable of providing information on the basis condition of the breath sample. These basis conditions can be compared to reference values and might enable the fat burning analyser to correct respectively correlate the sampling signal, detection signal and/or output signal to obtain realistic information on the fat burning intensity of the user. The basis conditions can be the pressure, the humidity, the temperature, the $CO_2$-concentration of the surrounding air and/or breath sample, for example before and/or after the breath pulse.

The sensor can be designed as a $CO_2$-sensor, wherein the $CO_2$-sensor can be arranged in the sampling part and is capable of providing information on the portion of the breath sample to be analysed. This allows to analyse specifically the end-tidal portion of the breath sample, which includes relevant information on the fat burning intensity of the user.

Furthermore, it is possible that the humidity sensor can also determine information in the relative humidity (RH) of the air before and/or after the breath pulse. Such an information can be used to evaluate the detection signal in a more precise manner. In particular the detection signal can be influenced by the relative humidity of the surrounding air. Therefore, a determination of the relative humidity before and/or after the breath pulse can enable the processing unit to correct i.e., to evaluate, the precise acetone presence (in particular acetone concentration) from the detection signal.

The flow sensor can also determine/provide information on the flow of the breath pulse. Such an information can be used to evaluate the volume of the breath sample, when taking into account the duration of the breath pulse. This can enable for an indication of the end-tidal portion of the breath sample.

The temperature sensor can determine information on the temperature of the breath sample. Such an information can be used to correct measured values and can improve the reliability of the fat burning intensity.

The sensor can be designed as pressure sensor and the pressure sensor can be arranged close to an orifice. The orifice can be arranged at an inlet of the sampling chamber. The orifice influences the flow of the breath pulse into the fat burning analyser. The inlet can be capable to let the exhaled breath sample flow into the sampling chamber. As essentially a continuous flow of the breath is to be generated by the user the orifice can influences the flow of the breath pulse. Behind the orifice the pressure drops. Such a changing of the pressure in the sampling part can be detected by the pressure sensor and the information can be provided as a sampling signal. The target value for the change of the pressure, in particular the drop of the pressure, at the sampling part can, for example, be approximately 980 Pa. In other words: The pressure sensor can be equipped to provide a trigger signal based on/related to the end-tidal breath sample collection. For example from the pressure determined by the pressure sensor the volume of the collected breath sample can be determined. Once a certain volume corresponding to the end-tidal breath sample is reached the trigger signal can be provided.

Furthermore, it is possible that the pressure sensor signal can be used to correct the detection signal. In particular the detection signal can be influenced by the flow. Therefore, a determination of the pressure during the breath pulse can enable the processing unit to correct, i.e., to evaluate the precise acetone presence (in particular acetone concentration) from the detection signal, namely to correct the flow dependence of the detection signal.

The sensor can be designed as a humidity sensor, wherein the humidity sensor can provide a sampling signal on the collection of the breath sample. The sampling signal can be used as a kind of trigger signal indicating the beginning of the breath sample collection. Such a signal may be triggered if the relative humidity of the breath sample is greater than 70%. The trigger signal can be utilised to recognise the collection of the breath sample. In other words: when the relative humidity (RH) rises above 70% the sampling part i.e., the fat burning analyser can recognise that the user is breathing into the fat burning analyser and that the breath sample is collected. To trigger i.e., to indicate and/or to recognise the collection of the breath sample, more robust than just using information on the RH is a combination of RH and a pressure signal. In particular, the humidity sensor can be equipped to provide a trigger signal on the breath sample collection if relative humidity of the breath sample is greater than 70%. The trigger signal can be provided by a combined sampling signal of the humidity sensor and the pressure sensor.

Additionally, the humidity sensor can also provide information on the relative humidity before and/or after the breath pulse or the breath sample collecting. This can enable the processing unit to correct the detection signal depending on the sampling signal provided before and/or after the collection of the breath sample. Meaning, that the humidity sensor can be equipped to essentially continuously providing information on the relative humidity of the air in the fat burning analyser. Thereby, a relative humidity of more than 70% is a good threshold for indicating the recognition of the breath sample collection.

As the humidity of the air surrounding the fat burning analyser has usually a smaller relative humidity (RH) than the breath sample of the user, the relative humidity RH is a reliable indicator of the starting of the breath pulse. It is possible to provide a sampling signal i.e., trigger signal, when the humidity target value of at least 70% is reached, otherwise no trigger signal is generated by the sampling part. It is possible that also further signals of the sampling part (for example from the pressure sensor) are provided once the humidity target value is reached and/or maintained. Also a rapid change of the humidity can indicate a breath sample.

The sensor can be designed as $CO_2$-sensor, wherein the $CO_2$-sensor can be capable of indicating the portion of the breath sample to be detected. The $CO_2$-sensor can be capable of triggering the duration and/or starting point of the detection of the breath sample. In particular the $CO_2$-sensor can provide the sampling signal i.e., a trigger signal, if the $CO_2$ concentration of the breath sample is greater than 3%, correlating with the desired $CO_2$ level of the end-tidal breath portion and/or mixed end-tidal breath portion. The triggering and recognition of the breath sample can be performed similar as with the humidity sensor, where constantly information on the $CO_2$ level can be provided by the $CO_2$-sensor, in particular also before and/or after the breath pulse. In particular, the $CO_2$-sensor can be equipped to provide a trigger signal on the breath sample collection if the $CO_2$ concentration of the breath sample is greater than 3%

The fat burning analyser can be equipped to guide the breath sample from the sampling part to the analysis unit. This guidance can be supported by a pump, a fan and/or a valve. Thereby it is possible that the valve only opens (to let the breath sample to the analysis unit) and the pump starts when the sampling signal indicates that the end-tidal breath portion can be detected and is arranged in the sampling part. Such a detection initiated by the sampling signal can also be called triggering.

Furthermore, the guidance of the breath sample can be realized by letting the breath sample diffuse form the sampling part to the analysis unit.

It might be also possible that the sampling part and the analysis unit are spatially separated or joint in a single chamber. The spatial separation has the advantage that the fat burning analyser can be configured to only receive the end-tidal breath portion due to triggered guidance upon evaluation of the sampling signal. The analysis unit is connectable to the sampling part allowing the guidance of the breath sample from the sampling part to the analysis unit.

The joint arrangement of the sampling part and analysis unit in a single chamber includes the advantage that the guiding of the breath sample is drastically simplified and an immediate detection and delivery of the detection signal can be improved.

The analysis unit can include an acetone sensor, wherein the acetone sensor is capable of detecting the acetone presence in the breath sample. This can enable the evaluation of the fat burning intensity of the user as the acetone concentration in the breath sample can be correlated to the fat burning intensity. The acetone sensor can be capable of detecting the acetone concentration, in particular the acetone concentration in a ppb-range enabling a detailed evaluation of the fat burning intensity of the user.

The acetone sensor can be capable of providing the detection signal upon exposure to acetone in the breath sample, in particular in the end-tidal portion of the breath sample. The detection signal can be a measure of the sensor output and/or sensor response. The sensor output and sensor response can be a sensor resistance, sensor current, sensor voltage, an optical signal and/or any other kind of output signal. Furthermore, it is possible that the detection signal includes processed information of the analysis unit in form of a sensor response, which can be measured as the sensor resistance, sensor current, sensor voltage, and/or any other kind of sensor output, changing upon exposure to acetone. The detection signal can be correlated with the acetone presence in the breath sample that can be derived from the sensor response. The sensor response can be measured as the sensor resistance, sensor current, sensor voltage, and/or any other kind of sensor output changing upon exposure to acetone. Naturally, the detection signal can be correlated with the acetone concentration in the breath sample. This correlation may be influenced by the sampling signal. The detection signal can be a resistance signal of the acetone sensor which can be processed in the processing unit. Furthermore, the detection signal can be a processed signal in form of a sensor response.

Suitable acetone sensors are known to the expert and can be commercially available. The acetone sensor can be a chemical sensor, in particular a chemo-resistive sensor, in particular a metal-oxide based sensor, in particular $WO_3$ sensor, in particular a epsilon-phase $WO_3$, in particular a Si-doped $WO_3$-sensor, in particular a Cr-doped $WO_3$-sensor, in particular a Si-doped and/or Cr-doped epsilon-phase WO3 sensor. Such an acetone sensor is quite sensitive to acetone and is only little influenced by the sampling condition.

The fat burning analyser can include an outlet that can be equipped to guide the breath sample collected by the fat burning analyser out of the fat burning analyser. Accordingly, the collected breath sample can be removed from the fat burning analyser and a new breath sample can be collected in the sampling part of the fat burning analyser, for example by breathing into the fat burning analyser via the inlet.

The fat burning analyser can include a mouthpiece that can be connected to the sampling part. The mouthpiece can enable the user to collect the breath sample with the fat burning analyser. This is possible by breathing via the mouthpiece into the sampling part. The mouthpiece can be designed such that breath is exhaled through the mouthpiece into the sampling part i.e., into the sampling chamber. The mouthpiece can be exchangeable and/or disposable.

The processing unit can be equipped to receive the sampling signal and/or the detection signal. The signals can include information on the flow, the relative humidity, the pressure, the time/duration, temperature, CO2-concentration and/or acetone concentration of the breath sample as indicated above. The flow can be correlated with the pressure drop measured by the pressure sensor. As explained above the pressure drop can appear upon impact of the breath pulse exhaled by the user.

The processing unit can include a memory. Furthermore, the processing unit can be equipped to recognise the breath sample due to the sampling signal and a comparison with corresponding target values, for example of a relative humidity greater than 70% and/or a pressure drop greater than approximately 100 Pa.

The processing unit can be capable of evaluating a signal of the acetone sensor upon exposure to acetone in the breath sample, namely the detection signal. The signal can be correlated to a resistance change of the acetone sensor, as the resistance change of the acetone sensor can be correlated with the acetone concentration. The evaluation might not only by based on the direct response of the acetone sensor to the breath sample but might also take into account the sampling conditions encoded in the sampling signal.

The processing unit can further include a memory unit. The processing unit can be capable of comparing the detection signal to a reference signal stored in the memory. The compare detection signal and/or corrected detection signal can be corrected by information provided from the sampling signal, for example the relative humidity. An evaluated detection signal can correspond to the detection signal compared to the reference signal. In other words: the detection signal is evaluated by taking into account information of the sampling signal. This enables to eliminate possible interference of other gases that do not change during the measurement and/or to provide a better comparability of the data between different users and/or for the same user on different training day.

Furthermore, the processing unit can be equipped to calculate the output signal from the detection signal and the reference signal. Thereby, the reference signal might differ from user to user and/or might even depend on the initial conditions for each individual user. The initial conditions can be at least one of the following: the sampling condition; the conditions before and/or after the sample collection; constitution of the user (being on diet, eating before sample collection, . . . ).

The processing unit can be designed to calculate correct the detection signal, wherein the sampling signal including information on the sampling conditions can be taken into account by evaluating the detection signal with respect to the sampling signal and/or reference signal. Thereby the reference signal can be calibrated to different detections conditions comparable to the sampling conditions of the breath sample.

The output signal can be displayed on a monitor indicating the fat burning intensity. Therefore the user is provided with an online, essentially immediate monitoring of its fat burning intensity. As explained above the fat burning intensity can correspond to a rather simple status information like fat burning: yes/no, or it can correspond to the degree of the fat burning.

The fat burning analyser can be equipped to enable the user to control the conditions of the breath sample exhalation by monitoring, evaluating and/or displaying the sampling signal and by providing a feedback loop enabling the user to reach and/or maintain a target value for the sampling. The feedback loop is capable of comparing the sampling signal to the target value or target values and providing the user with the corresponding information. For example, the target value and the corresponding sampling signal can be displayed simultaneously on a display, wherein the user can be encouraged to maintain or change his breathing.

At least part of the sampling part and/or the analysis unit can be heated. For example the fat burning analyser can at least partially heated above room temperature. In particular the fat burning analyser can be at least partially heated to at least 50° C., in particular at least 60° C. The heating of at least parts of the fat burning analyser, parts of the sampling part and/or the analysis unit reduce the possibility that components especially acetone is adsorbed to an inner surface of the fat burning analyser to the inner surface of the sampling part and/or analysis unit.

The fat burning analyser can be designed or equipped for real-time triggering of the collection of the desired end-tidal fraction of breath sample.

Generally, the sensor, in particular the sensor of the sampling part, can be equipped for recognising that a user is breathing through the analyser.

Additionally, the sampling part can include a valve equipped for controlling the air flow originating from breath exhaled into the breath analyser. Such a flow control can simplify the evaluation of the sampling signal and/or the detection signal as well as the corresponding output signal.

The breath pulse can be exhaled or let in the sampling part at a controlled flow, in particular at a flow of 50 mL/s. This can allow for a continuous reliable flushing of the sampling part with the breath sample. Furthermore, such a controlled flow rate allows the user to keep the exhaling for a desired duration (target duration) as the user does not try to exhale a big amount at the beginning of the breath pulse.

The fat burning analyser can be used for monitoring a fat burning rate of the user during exercise or during rest, for tailoring a diet based on monitored fat burning rate of the user, for monitoring fat burning metabolism of the user, supporting user on a diet based on the fat burning rate of the user for providing information of diagnoses related to the breath sample collected in the fat burning analyser, in particular for the diagnosis of diabetes.

A mouth piece can be compatible with the above described fat burning analyser. This enables the guidance of the breath sample directly into the analyser. Accordingly, a dilution or distortion/corruption of the breath sample can be minimized. This enables a reliable output of the fat burning intensity of the user.

The method for monitoring fat burn with a portable breath analyser as described above, wherein the method includes the following steps:
  providing a breath analyser as described above;
  letting the user exhale into the fat burning analyser, in particular into the sampling part;
  collecting a breath sample;
  providing the sampling signal from the sampling part;
  detecting the acetone presence, in particular the acetone concentration, in the breath sample with an acetone sensor in the analysis unit,
  providing a detection signal from the analysis unit,
  calculating the fat burning intensity from the sampling signal and/or the detection signal;
  generating an output signal corresponding to the fat burning intensity;
  displaying the output signal as a measure of the fat burning intensity.

The method can further include a step of helping the user to deliver a breath sample using a feedback loop and/or letting the breath sample out of the fat burning analyser to be prepared for a next measurement.

The calculation of the fat burning intensity can be based on the response ratio of the analysis unit and/or the processing unit.

The response ratio can depend on the current measurement and a reference signal. The reference signal does not have to depend on the condition before a breath pulse, but can be a breath pulse, e.g. at the beginning of a training.

General remark: the detection signal might correspond to an acetone presence and/or a detection signal might be the raw data of an acetone sensor, as for example a measured resistance (which is might be processed to an acetone presence, in particular the acetone concentration, in the processing unit).

Further preferred embodiments are evident from the dependent patent claims. Features of the method claims may be combined with features of the device claims and vice versa.

BRIEF DESCRIPTION OF THE DRAWINGS

The subject matter of the invention will be explained in more detail in the following text with reference to exemplary embodiments which are illustrated in the attached drawings, in which is shown.

DETAILED DESCRIPTION OF THE INVENTION

The reference symbols used in the drawings, and their meanings, are listed in summary form in the list of reference symbols. In principle, identical parts are provided with the same reference symbols in the figures.

Figure 1:
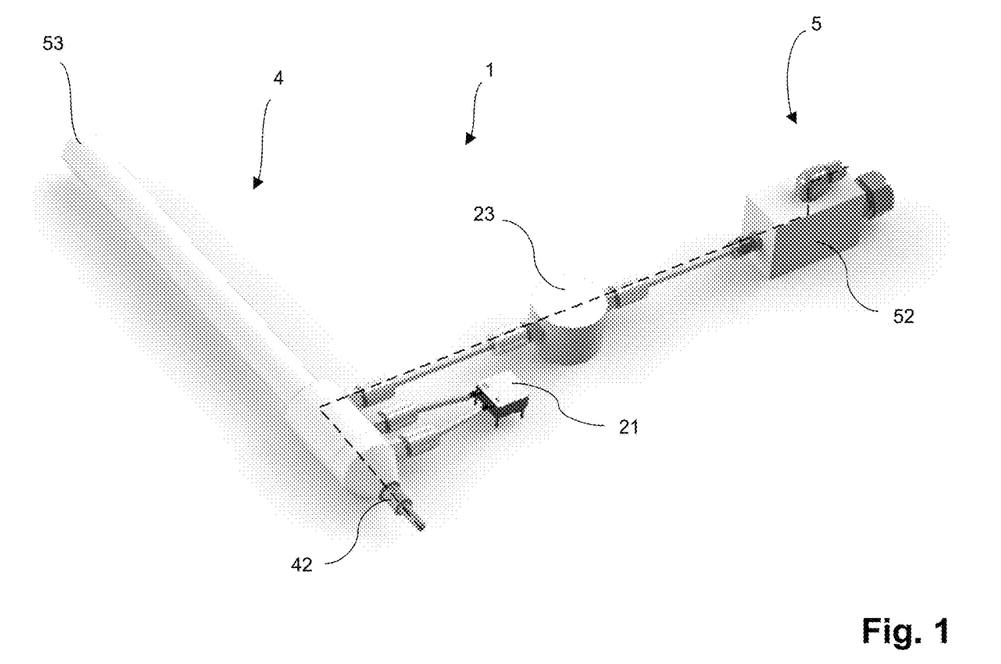
FIG. 1 shows a fat burning analyser 1.

FIG. 1 shows a fat burning analyser 1 including a sampling part 4, an analysis unit 5. Additionally, the fat burning analyser 1 includes a processing unit (not shown). The sampling part 4 includes a pressure sensor 21, a CO2-sensor 23. Furthermore, the sampling part 4 includes a sampling chamber 43 as well as a connection to a reference PTR-TOF-MS (specific mass spectrometer). The sampling part 4 and the analysis unit 5 are connected to each other.

Figure 2:
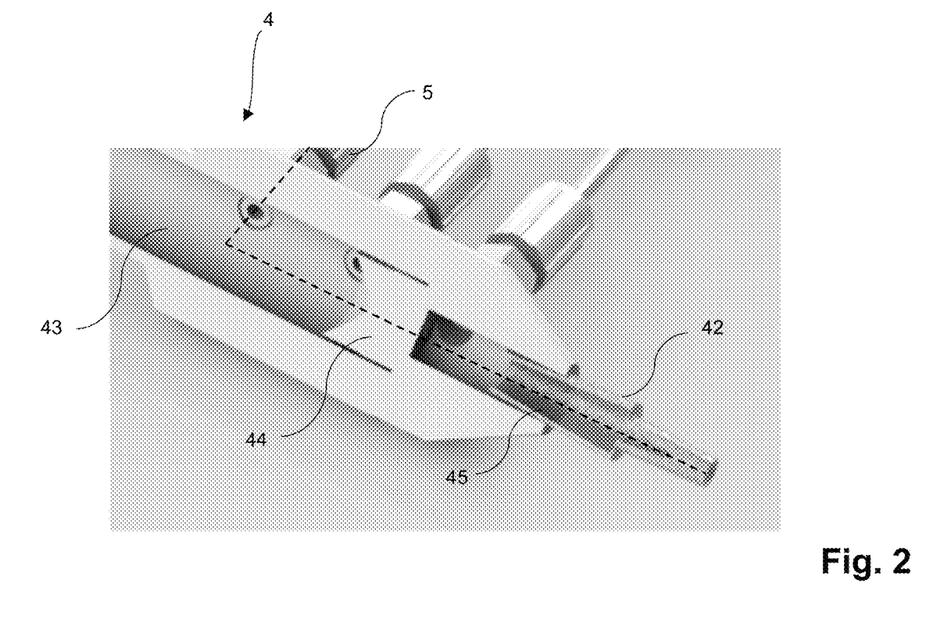
FIG. 2 is a cross-section of a sampling chamber 43 with an orifice 44.

FIG. 2 presents the cross-section of the sampling chamber 43 with an orifice for controllable flow and counter pressure.

FIGS. 1 and 2 show the fat burning analyser with its individual components. The newly developed fat burning analyser 1 can be split up into three parts. On one hand, there is a sampling part 4 and on the other hand there is an analysis unit 5 which is connected to the sampling part 4, and an additional processing unit (not shown). The fat burning analyser 1 is designed in such a way that single parts can be easily exchanged and optimized, making it flexible.

Breath Sampling/Collection of the Breath Sample 7

Breath is exhaled by the user, through a mouthpiece 42 (EnviTeC-Wismar GmbH, Germany) via an inlet 45 into the sampling chamber 43. The disposable mouthpieces 42 are exchanged after every breath test to avoid cross-contamination. The sampling chamber 43, made of Teflon® to inhibit analyte adsorption, has a diameter of 25 mm and a total length of 375 mm, giving a volume of 185 mL. On the other end (essentially opposite to the mouthpiece 42), the sampling chamber 43 is open to allow ambient air to be pushed out and most importantly, after a breath pulse end-tidal air (CO2 level>3%) to remain in the sampling chamber 43. The endogenous acetone (through interaction of air with blood in alveolar membrane) appears in highest concentrations in this end-tidal fraction of the breath sample 7. Thanks to the tube shaped design of the sampling chamber 43, the end-tidal sampling time can be prolonged. A prolongation of the end-tidal breath fraction results in better reproducibility. Breath pulses are exhaled by the user at a controlled flow of 50 mL/s. This is achieved by maintaining a pressure drop of 980 Pa, measured by a pressure sensor 21. Most users manage to keep this value comfortably for at least 30 s. A counter pressure resulting from the orifice 44 with an iteratively optimized diameter of 1.4 mm enables the user to exhale at a constant flow. By a 30 s exhalation pulse, end-tidal fraction is guaranteed to be captured, this means that the target value for the duration of the breath sample 7 collection is 30 s. The orifice 44 is tightly fixed inside the sampling part 4 close to the inlet 45 by a screwing mechanism. The transition from the orifice into the sampling chamber 43 is rounded and smooth to eliminate possible stagnation zones as well as analyte adsorption (adsorption of acetone). A differential pressure sensor 21 (SDP, Sensirion, Switzerland) after the inlet 45 allows to display the flow over the orifice 44 with direct feedback of the exhaled pressure drop. Thereby the pressure sensor 21 can provide the corresponding sampling signal 41. Monitoring and controlling the flow is essential for reproducible sampling or collection of the breath sample 7. Avoiding any breath condensation inside the sampling part 4, in particular inside the sampling chamber 43, is achieved by heating at least parts of the sampling part 4 with an insulated heating wire (TNI Medical, Germany) to 60° C.

Breath Analysis

A pump (SP 135 FZ, Schwarzer Precision, Germany) with a constant flow rate of 130 mL/min (=1.6 V) continuously sucked the air i.e., the breath sample 7, from the sampling part 4, in particular from the sampling chamber 43, through a connection element, in particular a Teflon line (4 mm inner diameter), into the analysis unit 5. The connection element can also be heated to 60° C. by an insulated heating wire (TNI Medical, Germany) to avoid any water condensation as well as adsorption of analytes, in particular acetone. A CO2 sensor 23 (Cozir WR, CO2 Meter, USA) is used to differentiate breath portions and especially indicate the end-tidal fraction (>3% CO2) of the breath. After the CO2 sensor 23, breath flow can be directed through the connection element into a small T-shaped sensor chamber described in detail elsewhere, where the acetone sensor 52, in particular a Si:WO3 sensor, is fixed with a holder, in particular a Macor holder. The sensor acetone sensor 52 can be vertically aligned with respect to the flow direction. A power supply (Rohde & Schwarz HMC8042, HAMEG Instruments GmbH, Germany) can be used to heat the acetone sensor 52 to an operating temperature of approximately 350° C. and the response of the acetone sensor 52, in particular the film resistance of the Si:WO3 sensor, can be measured by a multimeter (Keithley 2700, Keithley Instruments Inc., USA). Heat-up procedure of the fat burning analyser 1 in general together with baseline stabilization normally can take 30 min. Sensor stabilization and recovery between breath pulses were performed with ambient air. The sensor response (S) is defined as follows:

$$S = \frac{R_{air}}{R_{breath}} - 1$$

where $R_{air}$ denotes the acetone sensor 52 response with surrounding air and $R_{breath}$ is the response after the acetone sensor 52 has been exposed to a breath exhalation pulse (breath sample 7).

Validation by PTR-TOF-MS

A highly sensitive PTR-TOF-MS (mass spectrometer) (PTR-TOF 1000, Ionicon Analytik GmbH, Austria), that has already been tested to monitor acetone in human breath, allowed simultaneous cross validation of the acetone sensor 52 results. To do so, the inlet capillary of the mass spectrometer was directly placed in front of the acetone sensor 52. The PTR-TOF-MS requires a constant flow rate of 70 mL/min. Therefore, the total sampling flow into the connector element was 200 mL/min. Acetone signals 51 were measured in units of counts per seconds at a mass to charge ratio of m/z=59.049. To take possible background fluctuations into account, ethanol and isoprene were also monitored at m/z=47.049 and 69.069, respectively. However, both isoprene and ethanol stayed well below 10 ppb during all measurements.

Tested Users and Protocol 20 healthy volunteers or users (13 male and 7 female) with an age span from between 20 and 33 years participated in this study. All were in a generally healthy condition, non-smokers and had a body mass index of between 18 and 28 kg m'. None of the tested users smoked. The user followed a well-defined protocol: After overnight fasting, weight and height were measured and three initial breath exhalation pulses (breath sample 7) are taken as reference. Subsequently, three intervals of 30 minutes cycling on a bicycle ergometer (E5, Kettler, Germany; power independent of pedal speed, heart rate measurement included) at an intensity of 40% $V_{O2}$,max (=62.6% of the maximum heart rate) are carried out. The heart beat rate was measured by a pulse belt (T34, Polar, Finland). Between the exercise periods and every 60 minutes in the subsequent three hours after the exercise, three breath samples 7, originating from individual breath pulses, (=one data point) were taken. So a total of seven data points can be collected over the measurement time. Throughout the whole measurement, the volunteers continued fasting and were only allowed to drink water. All of the 20 user also did a normal control test for determining and investigating the stimulation effect of physical activity on the fat oxidation metabolism. The normal control testing protocol remained the same with the exception that no exercise was done, meaning the user was resting. The breath of the users was analysed by the fat burning analyser 1. The information of interest was the change of the sensor 52 response over time for both the exercise test as well as the normal, resting control test. To eliminate the influence of the different individual breath acetone baselines and the influence of other gases (as the acetone sensor 52 is not perfectly selective), instead of looking at absolute values for the sensor 52 response and the breath acetone concentration, the sensor 52 response ratio and breath acetone ratio with regard to the initially obtained value were analysed.

$$\text{sensor response ratio} = \frac{S}{S_{initial}}$$

$$\text{breath acetone ratio} = \frac{\text{breath acetone concentration}}{\text{breath acetone concentration}_{initial}}$$

The acetone sensor 52 can be calibrated before and after actual breath sample 7 tests. Calibration can be done with three breath relevant acetone concentrations of 420, 770 and 1360 ppb. Simulated breath pulses were given by admixing acetone (10 ppm in N2, Pan Gas 99.999%) to a carrier gas, consisting of synthetic air (Pan Gas, 99.999%) at 90% RH. The desired humidity level was obtained by mixing dry synthetic air with moist synthetic air obtained from a water bubbler. Mass flow controllers (Bronkhorst, Netherlands) were connected to the disposable mouthpiece 42 via a Teflon connector, through which the gas mixture was supplied at a flow rate of 1 L/min. The sensor 52 stabilized in ambient air with a constant flow of 130 mL/min.

Fat Burning Analyser 1 Characterisation

Figure 3:
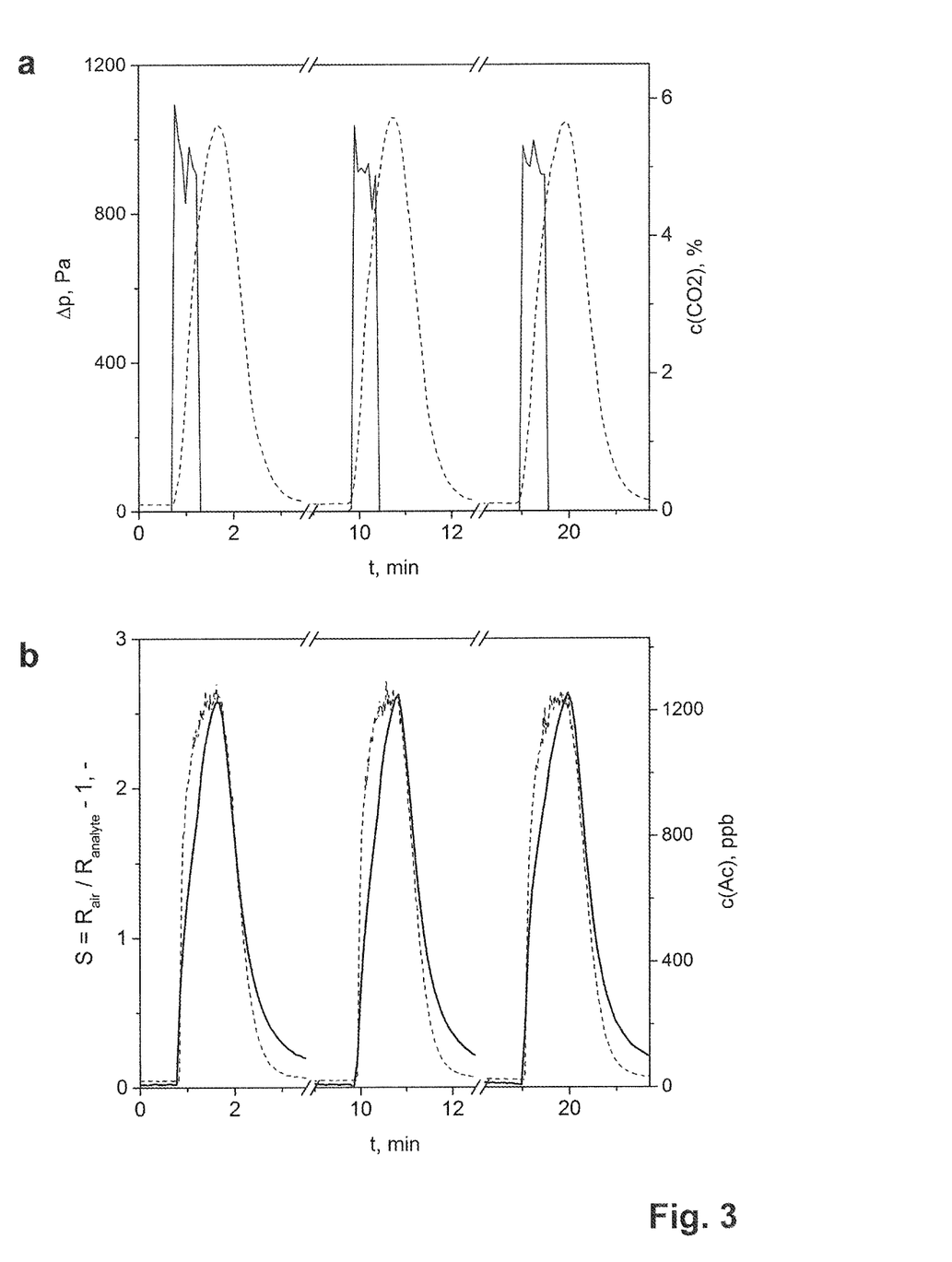
FIG. 3 shows the sampling conditions and detection signal 51 for three breath pulses.

FIG. 3 shows the sampling conditions (FIG. 3*a*) and detection signal 51 (FIG. 3*b*) for three breath pulses.

Pressure Sensor 21 and Pressure Drop

Figure 4:
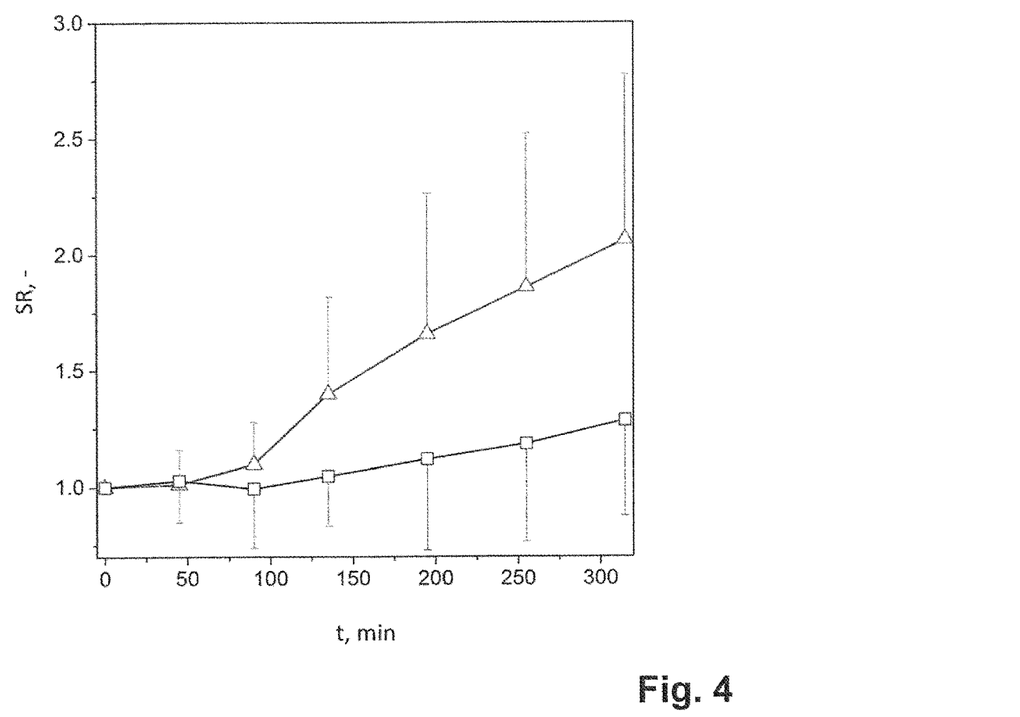
FIG. 4 shows sensor response ratios (SR) over time for 20 user.

The pressure sensor 21 is arranged in the sampling part 4 close to the orifice 44. In FIG. 3*a* the pressure drop (Δp) over the orifice 44 is plotted over time (t) for three exhalation pulses for three breath sample 7 collections. A digital readout, meaning the sampling signal 41, gives direct feedback of the achieved value while exhaling on breath sample 7 collection. It can be seen from the graph that exhaling for 30 s is possible and the pressure sensor 21 shows fast (<2 s) recovery times. The duration of the breath sample 7 collection is represented as striped area for the first breath pulse. The desired pressure drop values can be maintained by the user within ±100 Pa. Typically, the pressure drop of the first breath pulse is slightly too high at about 1100 Pa. Due to the direct feedback originating for the sampling signal 41, an adaption can be made within the pulse. By looking at the evolution of the three pulses, the normally observed training and learning effect is visible with the last pulse showing the smallest deviation range. The required target value of the pressure drop of 980 Pa corresponds to a controlled exhalation flow of 50 mL/s which is indicated by the horizontal dashed line in FIG. 4*a*.

CO2 Concentration

FIG. 3a (right scala) shows CO2 concentration (c(CO2)) peaks for the same breath pulses as a function of time, depicted as dashed line. During a breath pulse, the CO2 concentration increases. The three pulses show good reproducibility with respect to the peak value as well as the length. Concentration peaks are located between 5 to 6%. The similar values are reported in literature. The CO2 sensor enables determination of the end-tidal fraction of the breath (CO2>3%—represented as horizontal dashed line), where acetone appears in highest concentrations. By looking at the graph, it can be seen that for an exhalation time of 30 s, breath of the end-tidal fraction can be sampled for more than 60 s. Due to the advantageous design of the sampling chamber 43, the sampling time and exposure time of the Si:WO3 sensor with the breath sample 7 can be significantly prolonged. A delay time of 3 seconds with respect to the pressure sensor is measured. This can be explained by the fact that the breath sample 7 first needs to travel the connection element of a length of 600 mm to reach the CO2 sensor.

Acetone Sensor 52 Response and MS Validation

To further characterize the fat burning analyser 1, acetone sensor 52 response (S; left axis) and acetone concentration (c(ac); right axis) are shown for three exhalations in FIG. 3b. The solid line represents the acetone sensor 52 response while the dashed line stands for the acetone calibrated concentration determined by mass spectrometer measurements of the same breath sample 7. Sensor 52 responses show good reproducibility, although the sensor 52 does not seem to perfectly stabilize and reach steady-state. Furthermore, the acetone sensor 52 integrated into the sampling part 4 of the fat burning analyser 1 showed larger response times of 27 s compared to a value of 12 s in literature. This might be due to the mouth-to-sensor path distance of approximately 700 mm, whereas offline breath analysis with minimal mouth-to-sensor path was done with Tedlar Bags in literature. The sensor 52 and mass spectrometer start responding at the same time, but the MS response is faster, has a longer peak plateau and recovers faster to the baseline than the sensor 52 does. The sensor 52 reaches its peak when the MS signal already started decreasing again. The peak values measured by the MS also remain the same for all 3 pulses. Hence, it can be said that the fat burning analyser 1 enables prolonged, reproducible breath analysis.

Breath Sample 7 Characterization with Acetone Sensor 52 and Mass Spectroscopy The fat burning analyser 1 is applied to monitor breath acetone of 20 volunteers/user. Each user was tested twice: one time with initial exercise to stimulate fat burn, and thus increase acetone excretion, and another time remaining at rest throughout the experiment (control). FIG. 4 shows the acetone sensor response ratio (SR) over time (t) when tested with initial exercise (triangles) and control (squares). Note that ratios (SR) are used to normalize all volunteers to their initial sensor response (at t=0) for better comparability, where t is the time. When testing the 20 users with initial exercise, the sensor detects an onset of increasing acetone levels after 60 min (in average) and indicates a steady increase until the end of the experiment. Increasing breath acetone concentrations during and after exercise are expected and they had been observed also in other studies during cycling and walking. They reflect enhanced fat metabolism where acetone is released as by-product. In contrast during the control measurements, the fat burning analyser 1 i.e., the acetone sensor 52 detects only small breath acetone increase towards the end the measurement.

Figure 5:
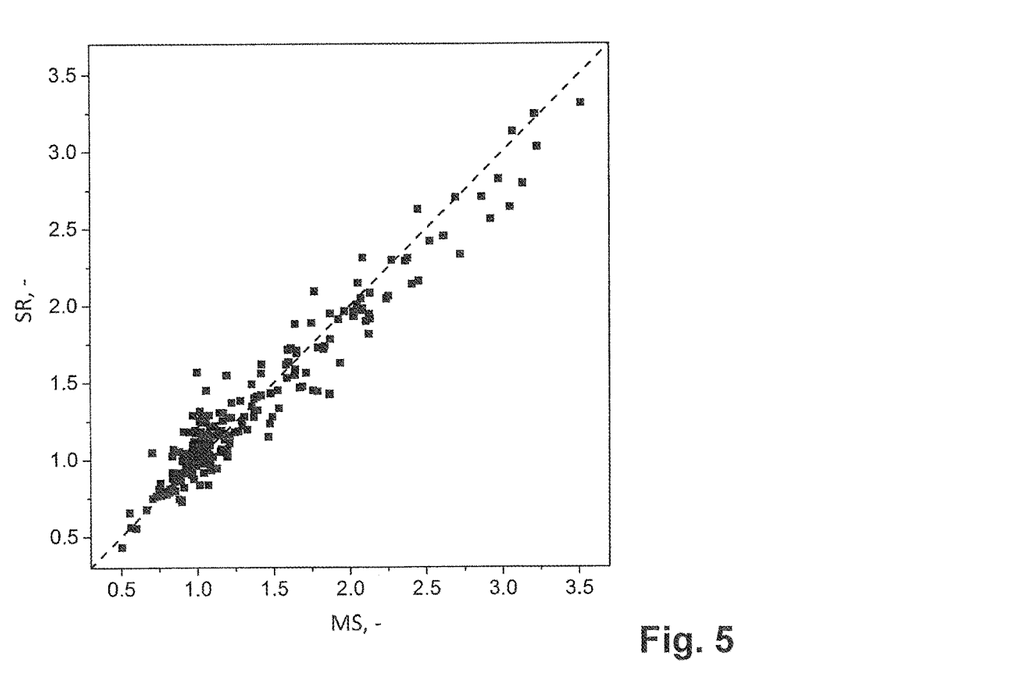
FIG. 5 shows a scatter plots of the acetone sensor 52 response ratios (SR) of the Si:WO3 sensor 52 and the breath acetone ratios obtained by a mass spectrometer (MS).

Note that the variation between volunteers (error bars) is rather large in both scenarios, as expected from usual biological variability including different fitness conditions of the users. To confirm the sensor's 52 accuracy for breath acetone detection, all breath samples are analysed simultaneously by state-of-the-art high-resolution mass spectrometer, in particular a PTR-TOF-MS31. FIG. 5 shows the scatter plot for the acetone sensor response (SR) and concentration (MS) ratios for all 280 analysed breath samples. Both instrument correlate strongly evidencing that the sensor 52 is a reliable tool to detect and monitor breath acetone accurately, that is remarkable considering its simplicity and compactness. In fact, the corresponding Pearson's (r) and Spearman's ($\rho$) correlation coefficients are 0.968 and 0.876, respectively.

Conclusion

The fat burning analyser 1 has been disclosed and characterized. It has been shown that reproducible and controllable sampling/sample collection with respect to CO2 concentration and/or flow is enabled. Especially, triggered and prolonged sampling of the end-tidal fraction of human breath can be achieved by utilising the sampling signal 41 of the sampling part. The portable sampling part 4 in combination with an analysis unit 5, in particular a acetone sensor 52, in particular a Si-doped WO3 flame-made sensor, can be successfully applied to display breath acetone dynamics not only during physical activity on a bicycle ergometer, but also in post exercise and normal control measurements providing information of the fat burning intensity as described above. An average 2.5-fold breath acetone increase after 90 min exercising followed by 3 h post exercise fasting has been found. During the normal control measurements, acetone concentrations remained on the initial levels. Sensor 52 measurements have been simultaneously cross-validated by a sophisticated mass spectrometer, in particular PTR-TOF-MS. The sensor response ratio results correlated well (r=0.968) with breath acetone ratio values. Therefore, the clear influence of exercise, tested on 20 healthy users after overnight fasting, on breath acetone concentration was detectable by the portable acetone sampler. As soon as the glucose storages are used up, the fat oxidation metabolism becomes the primary energy source. In summary, a fat burning analyser 1 is disclosed to accurately deliver information on the onset and behaviour of the individual breath acetone dynamics, which are directly linked to the fat oxidation metabolism, meaning the fat burning intensity. The gained insights reveals promising potential for the further development and miniaturization of this breath sampler and to finally allow end application for daily use.

While the invention has been described in present preferred embodiments of the invention, it is distinctly understood that the invention is not limited thereto, but may be otherwise variously embodied and practised within the scope of the claims.

The invention claimed is:

1. A portable fat burning analyzer for monitoring a fat burning intensity of a user from a user's breath, the analyzer comprising:
   a sampling part,
   an analysis unit and
   a processing unit;
   wherein the sampling part is equipped for collecting a breath sample from the user,
   wherein the sampling part is equipped for collecting information on the conditions of the breath sample collection, wherein the sampling part is equipped to provide a sampling signal correlated to the collection condition;

wherein the sampling signal is capable of indicating the beginning of an end-tidal portion of the breath sample;

wherein the analysis unit is equipped to provide a detection signal corresponding to an acetone presence in the collected breath sample of the end-tidal portion of the breath sample; and wherein the sampling part and the analysis unit are spatially separated and equipped to guide the breath sample from the sampling part to the analysis unit; and wherein the analysis unit is configured to receive the end-tidal portion of the breath sample due to triggered guidance upon indication of the beginning of the end-tidal portion of the breath sample by the sampling signal;

wherein the processing unit is equipped to receive the sampling signal and/or detection signal and to evaluate the sampling signal and/or the detection signal and to provide an output signal correlated to the fat burning intensity of the user.

2. The portable fat burning analyzer according to claim 1, wherein the fat burning intensity of the user is provided reproducibly based on the information of the collection condition provided by the sampling signal.

3. The portable fat burning analyzer according to claim 1, wherein the sampling signal is capable of triggering the detection signal.

4. The portable fat burning analyzer according to claim 1, wherein the sampling signal is capable of indicating a breath sample.

5. The portable fat burning analyzer according to claim 1, wherein the sampling signal comprises information on at least one of the following quantities: pressure, time/duration of the breath sample, volume of the breath sample, flow of the breath sample, temperature, $CO_2$-concentration and/or humidity of the breath sample.

6. The portable fat burning analyzer according to claim 1, wherein the processing unit can be equipped to recognize the breath sample due to the sampling signal and its comparison with corresponding target values.

7. The portable fat burning analyzer according to claim 1, wherein the sampling part is equipped for enabling the user to reach and/or maintain a target value and/or target duration for collection of a breath sample of the user.

8. The portable fat burning analyzer according to claim 1, wherein the sampling part comprises a sampling chamber for collecting the breath sample.

9. The portable fat burning analyzer according to claim 1, wherein the sampling part comprises a sampling chamber equipped for buffering the breath sample.

10. The portable fat burning analyzer according to claim 1, wherein the sampling part comprises an inlet and/or an outlet,
wherein the user breathes through the inlet into the sampling part and the breath flowing through the sampling part is guided to the outlet and allowing air to be pushed out of the sampling part and to allow mixed end-tidal portion of the breath sample to remain in the sampling part.

11. The portable fat burning analyzer according to claim 1, wherein the sampling part comprises a sensor equipped for providing information on the condition of the breath sample collection.

12. The portable fat burning analyzer according to claim 11, wherein the sensor is designed as a pressure sensor, a humidity sensor, a temperature sensor, a flow sensor and/or a $CO_2$ sensor.

13. The portable fat burning analyzer according to claim 11, wherein the sensor is designed as at least one of:
a pressure sensor being arranged in the sampling part and capable of providing information on the exhalation intensity and/or exhalation volume of the user;
a humidity sensor being arranged in the sampling part and capable of providing information on the sampling condition of the breath sample; and
a $CO_2$ sensor being arranged in the sampling part and capable of providing information on the portion of the breath sample to be analyzed;
a flow sensor being arranged in the sampling part and capable of providing information on the flow of the breath sample,
a temperature sensor being arranged in the sampling part and capable of providing information on the temperature of the breath sample.

14. The portable fat burning analyzer according to claim 11, wherein the sensor is designed as pressure sensor and wherein the pressure sensor is arranged close to an orifice, wherein the orifice is arranged at an inlet of the sampling chamber.

15. The portable fat burning analyzer according to claim 11, wherein the sensor is designed as humidity sensor and wherein the humidity sensor provides a sampling signal on the collection of the breath sample.

16. The portable fat burning analyzer according to claim 11, wherein the sensor is designed as CO2 sensor and wherein the CO2 sensor is capable of indicating the portion of the breath sample to be detected.

17. The portable fat burning analyzer according to claim 11, wherein the sensor is capable of triggering the duration and/or starting point of the detection of the breath sample.

18. The portable fat burning analyzer according to claim 1, wherein the analysis unit comprises an acetone sensor, wherein the acetone sensor is capable of detecting the acetone presence in the breath sample,
wherein the acetone sensor is capable of providing the detection signal upon exposure to acetone present in the breath sample.

19. The portable fat burning analyzer according to claim 18, wherein the acetone sensor is a chemical sensor.

20. The portable fat burning analyzer according to claim 1, wherein the processing unit is equipped to receive the sampling signal and/or the detection signal, said signals comprising information on the flow, the relative humidity, the pressure, the time/duration, temperature, $CO_2$-concentration and/or acetone concentration of the breath sample.

21. The portable fat burning analyzer according to claim 1, wherein the processing unit further comprises a memory unit, wherein the processing unit is capable of comparing the detection signal to a reference signal stored in the memory.

22. The portable fat burning analyzer according to claim 1, wherein the output signal is notified on a monitor, by an audio signal, visual signal and/or by vibration indicating the fat burning intensity.

23. The portable fat burning analyzer according to claim 1, wherein the fat burning analyzer is equipped to enable the user to control the conditions of the breath sample exhalation by monitoring the sampling signal and by providing a feedback loop enabling the user to reach and/or maintain a target value for the sampling.

24. The portable fat burning analyzer according to claim 1, wherein at least part of the sampling part and the analysis unit is heated.

25. A method of using a fat burning analyzer according to claim 1, comprising the step of:
- monitoring a fat burning rate of the user during exercise or during rest,
- monitoring the fat burning metabolism of the user,
- tailoring a diet based on a monitored fat burning rate of the user,
- supporting user on a diet based on the fat burning rate of the user, and/or
- providing information of diagnosis related to the breath sample collected in the fat burning analyzer.

26. A mouth piece compatible with a fat burning analyzer according to claim 1.

27. A method for monitoring fat burn with a portable fat burning analyzer according to claim 1, wherein the method comprises the following steps:
- providing the fat burning analyzer according to claim 1;
- letting the user exhale into the fat burning analyzer;
- collecting a breath sample;
- providing the sampling signal from the sampling part;
- guiding the breath sample from the sampling part to the analysis unit;
- detecting presence of acetone in the breath sample with an acetone sensor in the analysis unit,
- providing a detection signal from the analysis unit,
- calculating the fat burning intensity from the sampling signal and/or the detection signal;
- generating an output signal corresponding to the fat burning intensity;
- displaying the output signal as a measure of the fat burning intensity.

* * * * *